United States Patent [19]
Yee

[11] Patent Number: 5,672,256
[45] Date of Patent: Sep. 30, 1997

[54] MULTI-ELECTRODE BIOSENSOR AND SYSTEM AND METHOD FOR MANUFACTURING SAME

[75] Inventor: Hee-Jin Yee, Seoul, Rep. of Korea

[73] Assignee: LG Semicon Co., Ltd., Chungcheongbuk-do, Rep. of Korea

[21] Appl. No.: 569,740

[22] Filed: Dec. 8, 1995

[30] Foreign Application Priority Data

Dec. 8, 1994 [KR] Rep. of Korea ................. 33335/1994

[51] Int. Cl.$^6$ ................................................. G01N 27/26
[52] U.S. Cl. ..................... 204/403; 204/415; 204/412; 204/406; 435/817; 435/289.1
[58] Field of Search ..................... 204/403, 406, 204/412, 415; 435/817, 288, 291

[56] References Cited

U.S. PATENT DOCUMENTS

| | | | |
|---|---|---|---|
| 5,120,421 | 6/1992 | Glass et al. | 204/406 |
| 5,556,533 | 9/1996 | Nozoe et al. | 204/403 |
| 5,571,395 | 11/1996 | Park et al. | 204/403 |

*Primary Examiner*—Bruce F. Bell
*Attorney, Agent, or Firm*—Morgan, Lewis and Bockius, LLP

[57] ABSTRACT

A multi-electrode biosensor for sensing a material present in a sample includes a substrate, a plurality of working electrodes formed on the substrate, a counter electrode formed on the substrate, and a reference electrode formed on the substrate.

15 Claims, 6 Drawing Sheets

F I G.6a
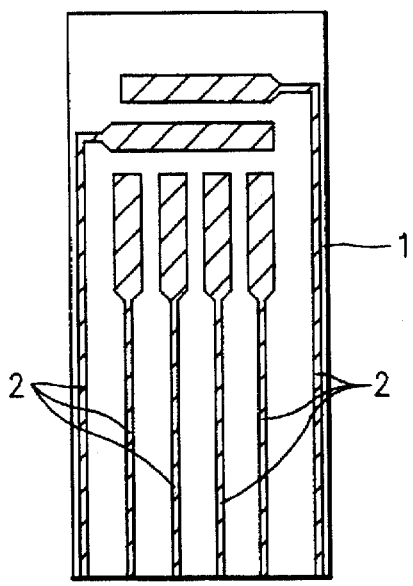
F I G.6b
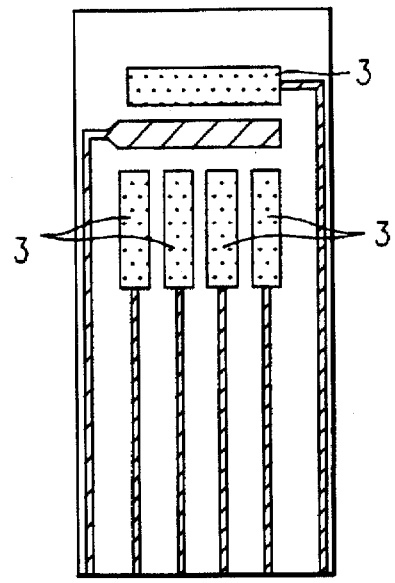
F I G.6c
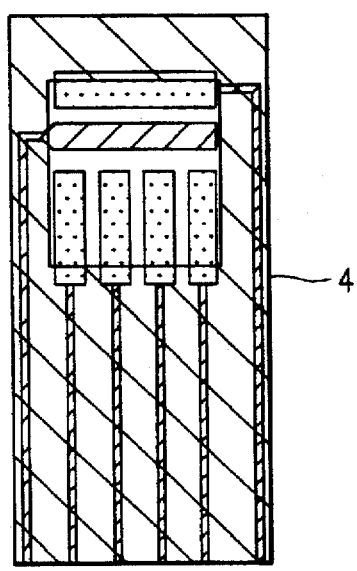
F I G.6d
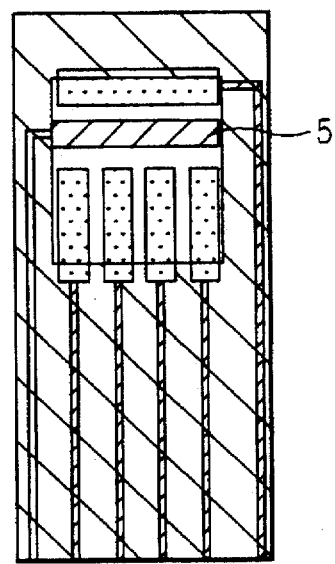

F I G.6e
F I G.6f
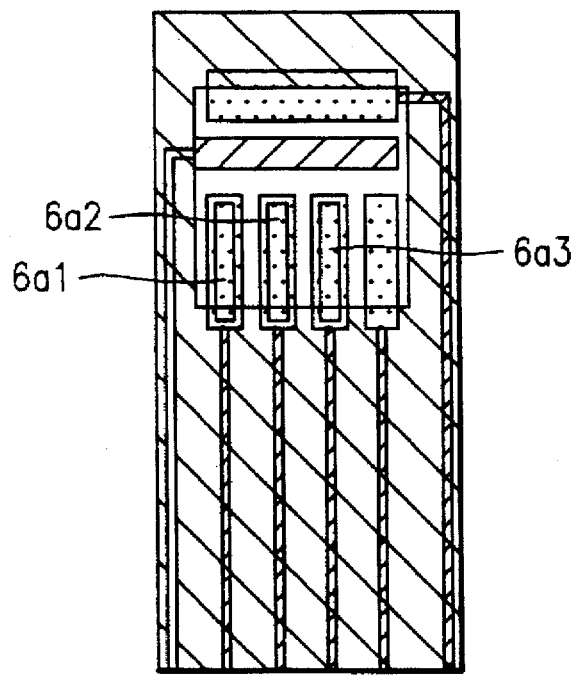
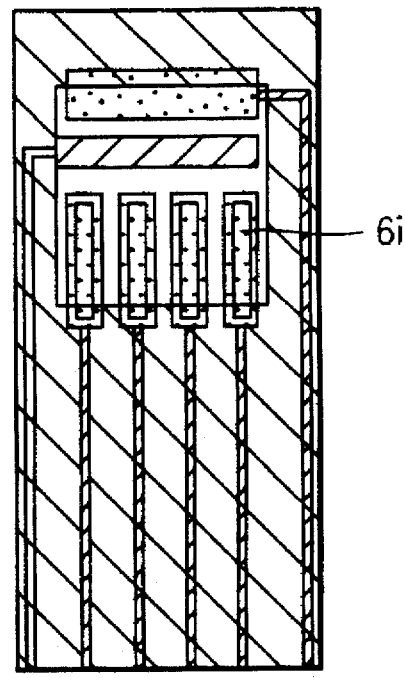

FIG.7

| ethanol concentration (ppm) | responsive current(μA) | |
|---|---|---|
| | multi-electrode type | none multi-electrode type |
| 21 | 1.550±0.045(2.90%) | 1.590±0.083(5.23%) |
| 167 | 4.340±0.118(2.73%) | 4.440±0.224(5.05%) |
| 665 | 6.570±0.166(2.90%) | 6.430±0.26(4.12%) |

*relative error $\left(\frac{\text{standard deviation}}{\text{average}} * 100\right)$

MULTI-ELECTRODE BIOSENSOR AND SYSTEM AND METHOD FOR MANUFACTURING SAME

BACKGROUND OF THE INVENTION

1. Field of the Invention

The present invention relates to a biosensor.

2. Discussion of the Related Art

Generally, a biosensor for measuring a predetermined material includes a biomaterial that selectively reacts with the predetermined material. Such a biosensor has advantages over other physical or chemical sensors. However, due to the instability of biomaterials, the biosensor's reliability is reduced as measurements are repeated, thereby requiring frequent replacement of the sensing film.

Recently, with the introduction of thick-film device technology, mass production of low cost sensors has been achieved. Some sensors are now intended for one-time use and thus disposed after one measurement. One-time biosensors have taken the lead in development of biosensors.

Clinically, the accuracy of a measurement is important when trying to precisely measure a very small amount of a material. Unlike physical or chemical sensors, most biosensors cannot correct themselves after fabrication. Thus, to obtain measurements, sensors of one batch must have exactly the same characteristics. For instance, in the case of a biosensor using an enzyme, when hundreds of sensors are manufactured on a substrate using thick-film device fabrication technology, the respective enzyme sensing films must have exactly the same amount of enzyme and several cofactors. In addition, the relative molecular orientation of the enzymes and the cofactors must be the same.

In reality, these conditions are impossible to meet so that the calibration curve of any biosensor has a permissible error range. Among the products on the market, some have an error range of 10% or higher. A biosensor with an error range of 5–6% is regarded as a commercial success. However, in most cases, the acceptability of such error ranges significantly depends on the user's skills. The meaning of a measurement using an apparatus having an error range of 5–6% may depend on the measurement's peculiarity. For instance, in the case of a blood sugar measuring apparatus, a widely used piece of equipment, a user is interested in whether a measured value deviates is above or below a predetermined value (i.e., high or low blood sugar). Attention is not paid to its intermediate value or how much the measured value deviates from the predetermined value.

If sequential values are clinically important within a predetermined range, the error range available in the above cases cannot ensure its accuracy. In this case, the solution is to average several measurements with several sensors. This inconvenience may be accepted by hospitals but not by general users.

A conventional biosensor will be described with reference to the attached drawings. FIG. 1 is a plan view of a conventional biosensor. FIG. 2 is a sectional view of the conventional biosensor cut along line II—II of FIG. 1.

The conventional biosensor has a working electrode 12, a counter electrode 13, and a reference electrode 14 all formed on an insulating substrate 11. Here, working electrode 12 is formed at the center, counter electrode 13 and reference electrode 14 are formed on both sides of working electrode 12, and counter electrode 13 is formed wider than reference electrode 14.

For insulating substrate 11, $Al_2O_3$ or a polymer such as poly Vinyl Chloride (PVC), Polyethylene Terephthalate, polyester, or Polyethylene may be used. For working electrode 12 and counter electrode 13, a paste containing an electric conductor such as platinum (Pt) or carbon (C) may be printed.

For example, if Pt is used for working electrode 12 and counter electrode 13, screen printing is performed on an 86×84 mm alumina substrate using a metal screen of 250 mesh. Then, the resultant structure is dried for ten minutes at 100° C. and fired at 1,250° C. For reference electrode 14, silver (Ag) paste is printed and fired at 850° C. Otherwise, Ag paste having AgCl may be printed.

The arrangement of working electrode 12, counter electrode 13, and reference electrode 14 does not affect their characteristics. But, their areas and distances between one another are important because they greatly affect the electrodes' signal magnitude and noise level.

Sequentially, Ag/Pt paste is printed and fired to form a connection pad 15. Then, dielectric paste is printed and fired to form an insulating layer 16. On the insulating layer 16 and on working electrode 12, counter electrode 13 and reference electrode 14, immobilized enzyme layer 17 is formed according to a material to be measured.

As an example, to manufacture an ethanol biosensor for measuring the concentration of ethanol, an enzyme solution is prepared in such a manner that 20 mg of alcohol dehydrogenase and 6.6 mg of $NAD^+$ (β-nicotinamide-adenine dinucleotide) are dissolved in 1 ml of 0.1M phosphate buffer. Then, 1 ml of solution is prepared in which gelatin is 10% (w/v) in 0.1M KCl solution. Here, 1 ml of the previously prepared enzyme solution is mixed at 25° C.

Next, 5 µl of the mixed enzyme solution are dropped on the electrodes of the insulating layer 16, which is then dried to form immobilized enzyme layer 17 in which the enzyme and cofactors are fixed.

These conventional biosensors have the following drawbacks. As discussed above, the biosensors cannot correct themselves and have reduced reliability because of a single working electrode despite an error range permissible within a predetermined extent. For this reason, if sequential values are important clinically within a predetermined scope, a user inconveniently must average several measured values with the conventional biosensor.

SUMMARY OF THE INVENTION

Accordingly, the present invention is directed to a multi-electrode biosensor that substantially obviates one or more of the problems due to limitations and disadvantages of the related art.

An object of the present invention is to provide a multi-electrode biosensor in which several working electrodes are formed on a single substrate using a technique of miniaturization and mass production of biosensors so that one measurement produces multiple signals in response to the same measured material. The signals are processed through circuits to determine the average, thereby obtaining a single measurement as accurate as the average of several measurements using different sensors.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, the multi-electrode biosensor of the present invention comprises a substrate, a plurality of working electrodes formed on the substrate, a counter electrode formed on the substrate, and a reference electrode formed on the substrate.

To further achieve these and other advantages and in accordance with the purpose of the invention, as embodied and broadly described, the multi-electrode biosensor system of the present invention comprises a multi-electrode biosensor including a substrate, a plurality of working electrodes formed on the substrate, a counter electrode formed on the substrate, and a reference electrode formed on the substrate; and a processing circuit including an average summing portion for averaging signals from selected ones of the plurality of working electrodes.

To still further achieve these and other advantages and in accordance with the present invention, as embodied and broadly described, the method for manufacturing a multi-electrode biosensor of the present invention comprises the steps of forming a plurality of metal conducting paths on the substrate, forming a first base carbon electrode on a first selected one of the plurality of metal conducting paths to provide a counter electrode, forming at least second, third, and fourth base carbon electrodes on respective second, third, and fourth selected ones of the plurality of metal conducting paths, forming a reference electrode from a fifth selected one of the plurality of metal conducting paths, providing a bioactive material on at least the second and third base carbon electrodes to form active working electrodes, and providing a bioinactive material on the fourth base carbon electrode to form an inert working electrode.

In one aspect, the multi-electrode biosensor includes more than two active working electrodes for generating signals by reacting independently with the same material present in a sample, an inert working electrode for correcting a background signal, a counter electrode, and a reference electrode.

In another aspect, the method of fabricating a multi-electrode biosensor includes the steps of printing a metal conducting path on a substrate by a predetermined interval as many as four working electrodes, reference electrode, and counter electrode; thermally processing the substrate, printing a base carbon electrode at the end of the metal conducting paths corresponding to the working electrodes and reference electrode, and thermally processing the resultant structure; forming an insulating layer on the overall surface of the structure with opening a rectangular area of the insulating layer so that the ends of the metal conducting paths serving as the base carbon electrode and reference electrode are exposed; forming the reference electrode at the ends of the metal conducting paths; forming active working electrodes on the three base carbon electrodes corresponding to the working electrode; and forming an inert working electrode on the remaining base carbon electrode corresponding to the working electrode.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings:

FIGS. 6a–6f are plan views of the multi-electrode biosensor of FIG. 3 during respective manufacturing steps; and FIG. 7 is a table comparing the reproducibility of the multi-electrode biosensor of FIG. 3 with that of the conventional biosensor when respective concentrations of ethanol are measured.

DETAILED DESCRIPTION OF THE PREFERRED EMBODIMENT

Reference will now be made in detail to the preferred embodiment of the present invention, an example of which is illustrated in the accompanying drawings.

Generally, the biosensor of the present invention includes a plurality of electrodes, which simultaneously generate a plurality of respective signals from a single measurement of a sample. The simultaneously generated signals are averaged by a processing circuit, such as a multi-channel potentiostat.

Figure 1:
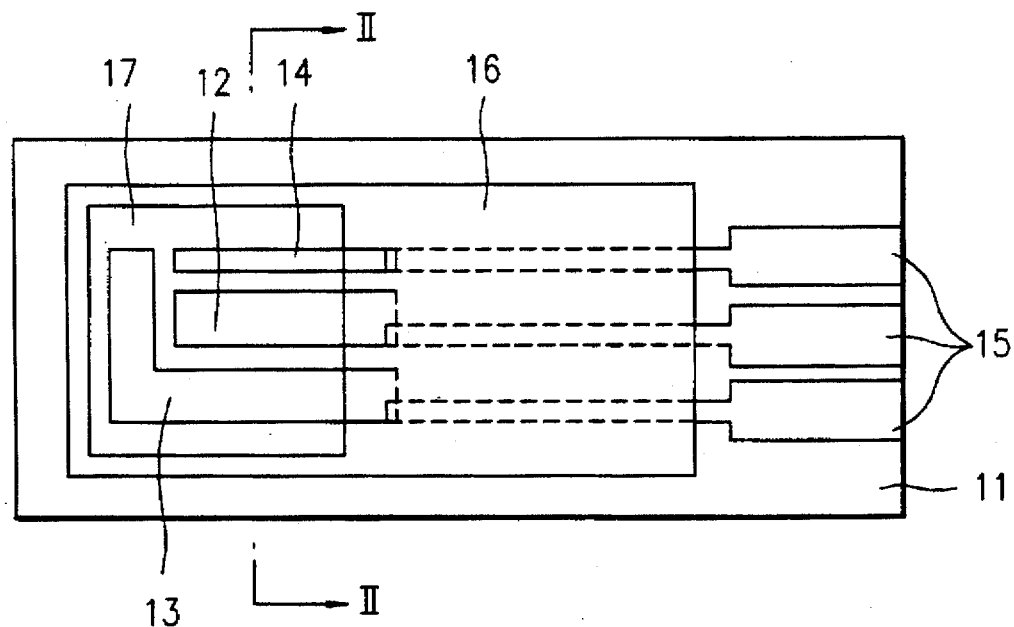
FIG. 1 is a plan view of a conventional biosensor.
Figure 2:
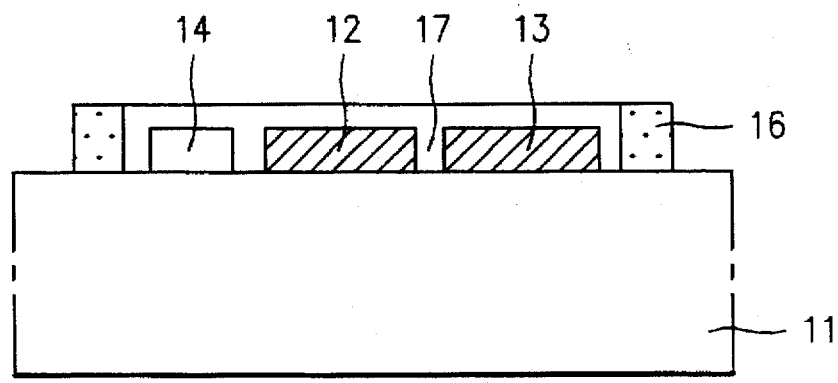
FIG. 2 is a sectional view of the conventional biosensor.
Figure 3:
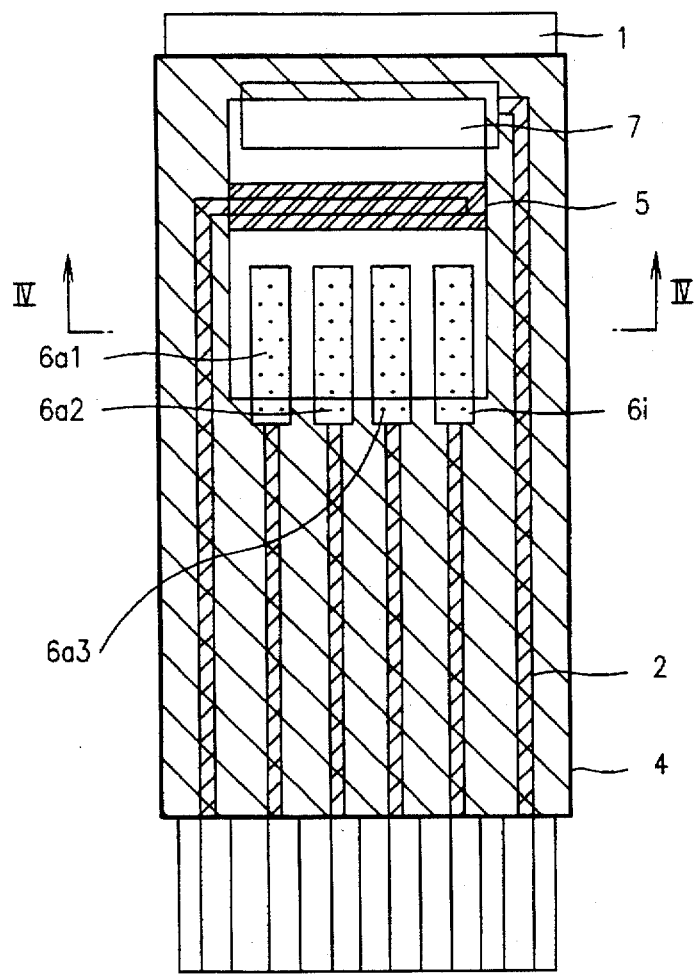
FIG. 3 is a plan view of one embodiment of a multi-electrode biosensor according to the present invention.
Figure 4:
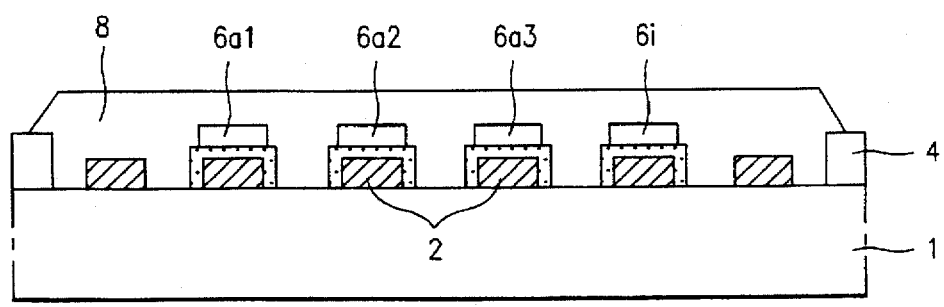
FIG. 4 is a sectional view of the multi-electrode biosensor of FIG. 3.

As shown in FIGS. 3 and 4, one embodiment of the multi-electrode biosensor of the present invention comprises four working electrodes 6a1, 6a2, 6a3 and 6i, a reference electrode 5, and a counter electrode 7. Of the working electrodes, electrodes 6a1, 6a2, and 6a3 are active working electrodes and electrode 6i is an inert working electrode. A processing circuit for averaging the signals output from the multiple electrodes of the multi-electrode biosensor is shown in FIG. 5.

Figure 5:
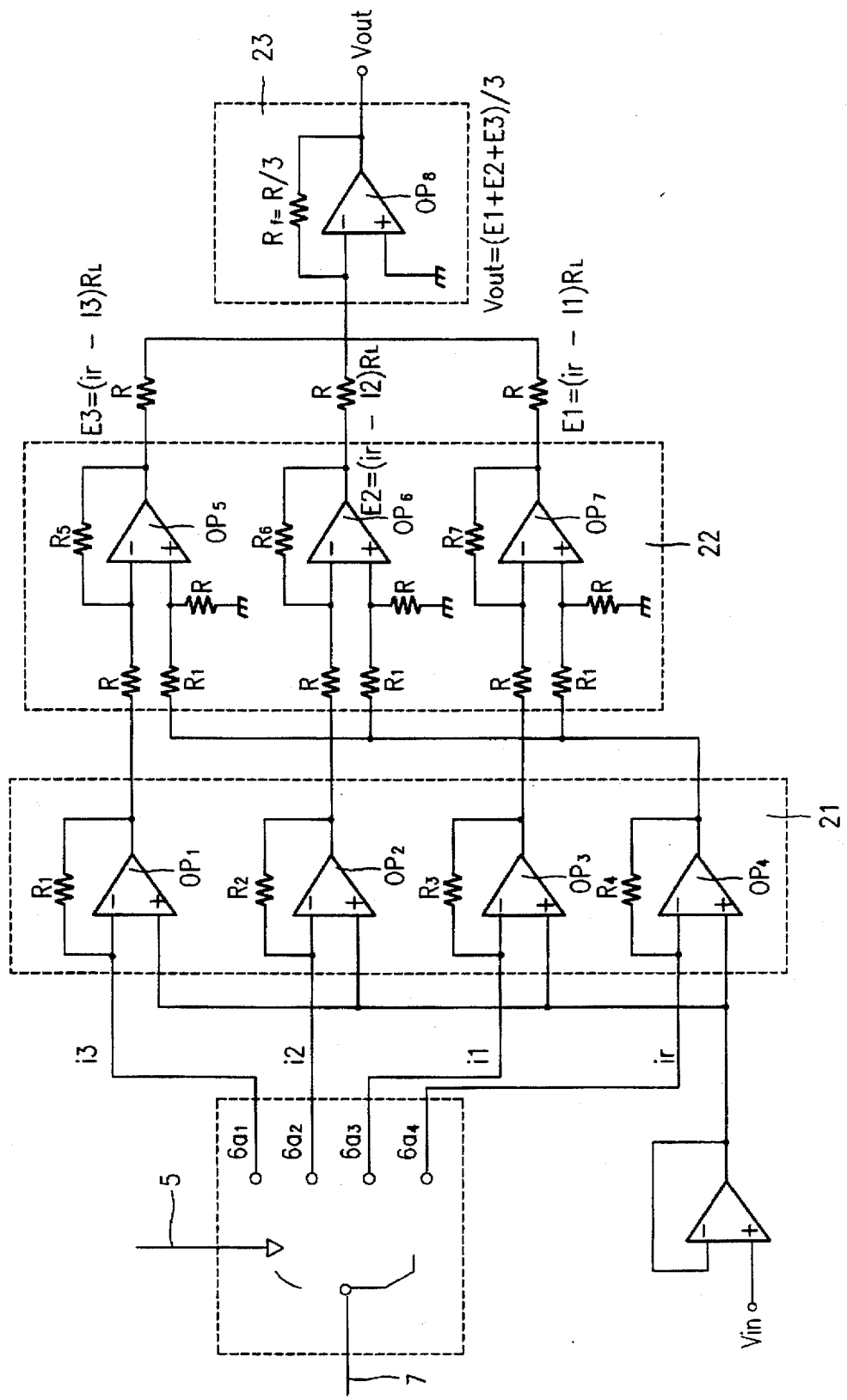
FIG. 5 is a circuit diagram for use with the multi-electrode biosensor of FIG. 3.

As shown in FIG. 5, the processing circuit comprises an amplifying portion 21 including amplifiers OP1, OP2, OP3 and OP4 and resistors R1, R2, R3 and R4, which are arranged as shown to amplify the signals output from active working electrodes 6a1, 6a2 and 6a3 and inert working electrode 6i by predetermined gains, a differential amplifying portion 22 including amplifiers OP5, OP6 and OP7 and resistors R5, R6 and R7, which are arranged as shown to differentially amplify the amplified signals of active working electrodes 6a1, 6a2 and 6a3 using the amplified signal of inert working electrode 6i as a reference signal, and an average summing portion 23 including an amplifier OP8 and resistor Rf, which are arranged as shown to sum the signals output from differential amplifying portion 22 and divide the summed signal by the number of active working electrodes, i.e., three, to thereby output their average. Here, reference signal $V_{in}$ of amplifying portion 21 operates the biosensor and serves to maintain a voltage between reference electrode 5 and the four working electrodes at $V_{TN}$.

A method of manufacturing the multi-electrode biosensor of FIGS. 3 and 4 will now be described.

As shown in FIG. 6a, silver conducting paths 2 are formed on a polyester substrate 1 for the four working electrodes, the reference electrode, and the counter electrode using thick film device technology.

As shown in FIG. 6b, the resultant substrate 1 is thermally processed for ten minutes at 110° C., base carbon electrodes 3 are printed at the ends of the silver conducting paths for the working electrodes and counter electrode, and the resultant structure is thermally processed. The base carbon electrode printed on the end of the silver path for the counter electrode has no layer piled thereon.

As shown in FIG. 6c, an insulating layer 4 is formed on the surface of the resultant structure except on at least portions of the base carbon electrodes 3 and except on at least a portion of the end of the silver conducting path for the reference electrode. For example, the open area may be rectangular as shown.

As shown in FIG. 6d, the resultant structure is immersed in 100 mM of $FeCl_3$ so that Ag/AgCl is formed at the exposed end of the silver conducting path for the reference electrode to complete the reference electrode 5.

As shown in FIG. 6e, as an ethanol biosensor manufacturing step, for example, 405 mg of alcohol dehydrogenase (ADH), 45 mg of $NAD^+$, 40 mg of DEAE-dextran, 400 mg of lactitol, and 1.28 g of carbon powder are put into a mortar with 4 ml of 2% hydroxyethyl cellulose. They are homogenized to form a bioactive paste which is printed on three of the base carbon electrodes to form active working electrodes 6a1, 6a2, and 6a3.

As shown in FIG. 6f, a bioinactive paste, such as bovine serum albumin having the same amount of the ADH used in FIG. 6e, is printed on the remaining base carbon electrode to form inert working electrode 6i.

To complete the multi-electrode biosensor for measuring ethanol vapor, a 6% hydroxyethyl cellulose paste is printed on the resulting structure to form an outer layer 8 (FIG. 4) to be used as a buffered electrolyte system.

FIG. 7 shows a table in which ethanol vapor is measured by the multi-electrode ethanol biosensor using the multi-channel potentiostat in order to examine its reproducibility. The results are compared with measurements using a conventional biosensor (non-multi-electrode type) having a working electrode, reference electrode, and counter electrode. As indicated in the table, the multi-electrode ethanol biosensor of the present invention has a smaller error range than that of the conventional non-multi-electrode biosensor. Therefore, the present invention yields excellent reproducibility.

As described above, in the present invention, several working sensors for generating a signal by reacting with a predetermined material are provided on a single sensor, thereby obtaining the effect of performing several independent measurements through a one-time measurement. This involves no requirement to average several measurements using respective sensors so that a user easily obtains a clinically important measurement value regardless of specialty or skill.

Therefore, the commercially useful scope of health self-diagnosing apparatuses for measuring only a value above or below a discontinuous value can expand to the clinical field which requires higher precision and continuous values become important. In addition, high reliability can be ensured in any precision measurement using a biosensor.

This invention can be employed in a thick-film biosensor using screen printing, a thin-film biosensor in which biomaterials, such as enzymes, antigens, antibodies, nucleic acids, and molecular receptors are fixed on the working electrodes, and in a biosensor having working electrodes with electrochemical, optical, and/or piezoelectric properties.

It will be apparent to those skilled in the art that various modifications and variations can be made in the multi-electrode biosensor and method for manufacturing same of the present invention without departing from the spirit or scope of the invention. Thus, it is intended that the present invention cover the modifications and variations of this invention provided they come within the scope of the appended claims and their equivalents.

What is claimed is:

1. A multi-electrode biosensor comprising:

a substrate;

a plurality of working electrodes formed on the substrate, the plurality of working electrodes including at least two active working electrodes and an inert working electrode, wherein the active working electrode includes a bioactive material and the inert working electrode is bioinactive;

a counter electrode formed on the substrate; and a reference electrode formed on the substrate.

2. The multi-electrode biosensor according to claim 1, wherein the biomaterial includes at least one of an enzyme, an antigen, an antibody, a nucleic acid, and a molecular receptor.

3. The multi-electrode biosensor according to claim 1, wherein the biomaterial has at least one of electrochemical, optical, and piezoelectric properties.

4. A multi-electrode biosensor system comprising:

a multi-electrode biosensor including;

a substrate, a plurality of working electrodes formed on the substrate, the plurality of working electrodes including at least two active working electrodes and an inert working electrode, wherein the active working electrode includes a bioactive material and the inert working electrode is bioinactive, a counter electrode formed on the substrate, and a reference electrode formed on the substrate; and a processing circuit including an average summing portion for averaging signals from selected ones of the plurality of working electrodes.

5. The multi-electrode biosensor system according to claim 4, wherein the plurality of working electrodes include at least two active working electrodes, and wherein the average summing portion averages signals from the active working electrodes.

6. The multi-electrode biosensor system according to claim 4, wherein the average summing portion includes an amplifier and resistor.

7. The multi-electrode biosensor system according to claim 4, wherein the processing circuit further includes an amplifying portion for amplifying signals from each of the plurality of working electrodes.

8. The multi-electrode biosensor system according to claim 7, wherein the amplifying portion includes, for each of the plurality of working electrodes, an amplifier and a resistor.

9. The multi-electrode biosensor system according to claim 7, wherein the processing circuit further includes a differential amplifying portion for differentially amplifying selected ones of the signals amplified by the amplifying portion.

10. The multi-electrode biosensor system according to claim 9, wherein the plurality of working electrodes include at least two active working electrodes and an inert working electrode, wherein the amplifying portion amplifies signals from the at least two active working electrodes and the inert electrode, and wherein the differential amplifying portion differentially amplifies the amplified signals from the active working electrodes using the amplified signal from the inert working electrode as a reference signal.

11. A method for manufacturing a multi-electrode biosensor on a substrate comprising the steps of:

forming a plurality of metal conducting paths on the substrate;

forming a first base carbon electrode on a first selected one of the plurality of metal conducting paths to provide a counter electrode;

forming at least second, third, and fourth base carbon electrodes on respective second, third, and fourth selected ones of the plurality of metal conducting paths;

forming a reference electrode from a fifth selected one of the plurality of metal conducting paths;

providing a bioactive material on at least the second and third base carbon electrodes to form active working electrodes; and providing a bioinactive material on the fourth base carbon electrode to form an inert working electrode.

12. The method according to claim 11, further comprising the step of providing an insulating layer except on at least portions of the at least first, second, third, and fourth base carbon electrodes and except on at least a portion of the fifth selected one of the plurality of metal conducting paths.

13. The method according to claim 11, wherein the step of forming the reference electrode includes the step of forming Ag/AgCl on the fifth selected one of the plurality of metal conducting paths.

14. The method according to claim 11, further comprising the step of providing an outer layer to be used as a buffered electrolyte system.

15. The method according to claim 11, wherein the step of providing the bioactive material on at least the second and third base carbon electrodes includes the step of applying a bioactive paste on at least the second and third base carbon electrodes, and wherein the step of providing the bioinactive material on the fourth base carbon electrode includes the step of applying a bioinactive paste on the fourth base carbon electrode.

* * * * *